United States Patent
Katayama

(10) Patent No.: US 7,542,401 B2
(45) Date of Patent: Jun. 2, 2009

(54) BIREFRINGENCE CHARACTERISTIC MEASURING METHOD, OPTICAL RECORDING MEDIUM AND OPTICAL INFORMATION RECORDING/REPRODUCING APPARATUS

(75) Inventor: Ryuichi Katayama, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 11/750,202

(22) Filed: May 17, 2007

(65) Prior Publication Data

US 2007/0214468 A1   Sep. 13, 2007

Related U.S. Application Data

(62) Division of application No. 10/704,631, filed on Nov. 12, 2003, now Pat. No. 7,272,091.

(30) Foreign Application Priority Data

Nov. 12, 2002  (JP) ............................. 2002-328702

(51) Int. Cl.
  *G11B 7/135* (2006.01)
(52) U.S. Cl. .................... 369/121; 369/275.5; 369/283; 369/286; 369/288
(58) Field of Classification Search ............. 369/275.5, 369/53.22, 283, 286, 288
  See application file for complete search history.

(56) References Cited

U.S. PATENT DOCUMENTS

| 5,257,092 | A | 10/1993 | Noguchi et al. |
|---|---|---|---|
| 5,481,530 | A * | 1/1996 | Ueda et al. ............... 369/275.1 |
| 5,644,562 | A | 7/1997 | de Groot |
| 5,917,791 | A | 6/1999 | Tsuchiya et al. |
| 6,137,626 | A | 10/2000 | Takaoka |
| 6,201,634 | B1 | 3/2001 | Sakuma et al. |
| 6,565,974 | B1 * | 5/2003 | Uchiyama et al. ........... 428/412 |
| 6,707,787 | B2 | 3/2004 | Yamasaki et al. |
| 6,743,527 | B2 * | 6/2004 | Hisada et al. ............ 428/846.9 |
| 6,764,737 | B2 | 7/2004 | Arakawa et al. |
| 6,986,861 | B2 | 1/2006 | Yamasaki et al. |
| 2002/0075795 | A1 * | 6/2002 | Yamasaki et al. ........... 369/283 |
| 2003/0053392 | A1 * | 3/2003 | Jeong ...................... 369/112.1 |
| 2004/0013076 | A1 * | 1/2004 | Funato et al. .......... 369/112.12 |
| 2004/0085875 | A1 | 5/2004 | Mizuno et al. |

FOREIGN PATENT DOCUMENTS

| JP | 61-149846 A | 7/1986 |
|---|---|---|
| JP | 63-61936 A | 3/1988 |
| JP | 64-013431 A | 1/1989 |

(Continued)

*Primary Examiner*—Wayne R Young
*Assistant Examiner*—Linh T Nguyen
(74) *Attorney, Agent, or Firm*—Sughrue Mion, PLLC

(57) ABSTRACT

Four types of optical systems, a polarization optical system including an objective lens having a high numerical aperture, a polarization optical system including an objective lens having a low numerical aperture, a non-polarization optical system including an objective lens having a high numerical aperture and a non-polarization optical system including an objective lens having a low numerical aperture, are selectively used at the time of irradiating light from a semiconductor laser on a target disk for measurement, and the in-plane birefringence characteristic and perpendicular birefringence characteristic of the target disk are separately acquired based on the amounts of received light obtained by measuring reflected light from the target disk by a photosensor.

2 Claims, 7 Drawing Sheets

FOREIGN PATENT DOCUMENTS

| | | |
|---|---|---|
| JP | 01-184444 A | 7/1989 |
| JP | 2-205755 A | 8/1990 |
| JP | 6-103252 B2 | 12/1994 |
| JP | 7-229828 A | 8/1995 |
| JP | 8-20358 B2 | 3/1996 |
| JP | 8-201277 A | 8/1996 |
| JP | 3011036 B2 | 12/1999 |
| JP | 2001-083042 A | 3/2001 |
| JP | 2001-296206 A | 10/2001 |
| JP | 2003-247934 A | 9/2003 |

\* cited by examiner

BIREFRINGENCE CHARACTERISTIC MEASURING METHOD, OPTICAL RECORDING MEDIUM AND OPTICAL INFORMATION RECORDING/REPRODUCING APPARATUS

BACKGROUND OF THE INVENTION

1. Field of the Invention

The present invention relates to a birefringence characteristic measuring method, an optical recording medium and an optical information recording/reproducing apparatus, and, more particularly, to a birefringence characteristic measuring method which can separately measure the in-plane birefringence and perpendicular birefringence in the birefringence characteristic of the protective layer of an optical recording medium, an optical recording medium which has a protective layer with an excellent birefringence characteristic and has an excellent recording/reproduction characteristic and an optical information recording/reproducing apparatus which uses the optical recording medium.

2. Description of the Related Art

According to the specifications for DVDs (Digital Versatile Disks) produced in 1996, the wavelength of a light source is 650 nm, the numerical aperture (NA) of an objective lens is 0.6, the thickness of a substrate which is the protective layer of an optical recording medium is 0.6 mm and the recording capacity of the optical recording medium with a diameter of 120 mm is 4.7 GBytes. As the bit length is 0.267 µm and the track pitch is 0.74 µm, the recording density is $1/(0.267 \times 0.74)$ bits/µm$^2$=3.3 Gbits/inch$^2$.

However, the present recording density of DVDs is insufficient to record and play back high-definition moving pictures for a long period of time. Recording and playback of high-definition moving pictures at a high quality requires a data transfer rate of at least 13 Mbits/sec. The recording density that is needed to record and play back moving pictures for 120 minutes at this data transfer rate is 13 Mbits/sec×120 minutes=11.7 GBytes. With the DVD standard, the recording density at this time is calculated to be 3.3 Gbits/inch$^2$×(11.7 GBytes/4.7 GBytes)=8.2 Gbits/inch$^2$.

To increase the recording capacity of an optical recording medium, it is effective to shorten the wavelength of a light source to be used in recording and playback. The recording capacity is inversely proportional to the square of the diameter of a focused spot formed on an optical recording medium and the diameter of the focused spot is proportional to the wavelength of the light source. That is, the recording capacity is inversely proportional to the square of the wavelength of the light source. Recently, semiconductor lasers with a wavelength of 405 nm or so, as described in Japanese Journal of Applied Physics, Vol. 39, Part 2, No. 7A, pp. L647 to L650, and lasers which uses second harmonics with a wavelength of 410 nm or so, as described in International Symposium on Optical. Memory 2001 Technical Digest, pp. 228 to 229, have achieved the practical levels.

With the DVD standard, the wavelength of a light source for achieving the recording capacity of 11.7 GBytes is 650 nm×√(4.7 GBytes/11.7 GBytes)=412 nm. Therefore, the use of the aforementioned semiconductor laser and the aforementioned laser using the second harmonics as a light source can record and play back high-definition moving pictures on and from an optical recording medium with a diameter of 120 mm, the same diameter as that of a DVD, for 120 minutes. As the numerical aperture (NA) of the objective lens can be 0.6 and the thickness of the protective layer of the optical recording medium can be 0.6 mm, both being the same as those of a DVD, the objective lens and optical recording medium can be fabricated by the same technology as used for DVDs. If the wavelength of the light source is made shorter than 412 nm and the numerical aperture (NA) of the objective lens is made higher than 0.6, the diameter of the focused spot becomes smaller, thus ensuring a recording capacity greater than 11.7 GBytes (higher recording density than 8.2 Gbits/inch$^2$).

While low-cost polycarbonate is generally used for a substrate which is the protective layer of an optical recording medium, the polycarbonate has birefringence. In an optical information recording/reproducing apparatus which records and plays back information on and from an optical recording medium, a polarization optical system which uses a combination of a polarization beam splitter and a quarter-wave plate is generally used to improve the utilization factor of light. In case where such a polarization optical system is used, if the protective layer of an optical recording medium has birefringence, the amount of received light of the photosensor which receives reflected light from the optical recording medium is reduced. Further, the peak intensity of the focused spot to be formed on the optical recording medium drops. The reduction in the amount of received light leads to a decrease in signal-to-noise ratio at the time of playback and the reduction in peak intensity leads to an increase in optical power needed.

According to the DVD specifications, therefore, a birefringence characteristic measuring method and the allowance for the birefringence are defined for the protective layer of an optical recording medium. FIG. 1 shows the structure of an optical system which is used in this measuring method. The structure of the optical system is described in the specifications for read-only DVD-ROM, "DVD Specifications for Read-Only Disc Part 1: PHYSICAL SPECIFICATIONS", the specifications for recordable DVD-R, "DVD Specifications for Recordable Disc Part 1: PHYSICAL SPECIFICATIONS", the specifications for re-recordable DVD-RW, "DVD Specifications for Re-recordable Disc Part 1: PHYSICAL SPECIFICATIONS" and so forth.

The light that is output from a laser 24 with a wavelength of 650 nm as the light source is linearly polarized by a polarizer 25, is converted to be circularly polarized by a quarter-wave plate 26 and is then irradiated on a disk 6 as an optical recording medium. The angle of incidence to the disk 6 is 7°. The reflected light from the disk 6 is received at a photosensor 29 via a rotation analyzer 27 and a collimator lens 28. As the reflected light from the disk 6 reciprocates the protective layer of the disk 6, it is influenced by the birefringence and is elliptically polarized. By rotating the rotation analyzer 27 to measure the amount of light received at the to photosensor 29, the ellipticity of the elliptically polarized light is measured and a birefringence-originated phase difference δ between two orthogonal polarized light components is acquired. Given that Δn is the birefringence, d is the thickness of the protective layer and λ is the wavelength of the light source, as $\delta = (2\pi/\lambda) \cdot \Delta n \cdot 2d$ is satisfied, the birefringence Δn can be acquired from the equation. The specifications of DVD-ROM, DVD-R and DVD-RW describe the allowance for birefringence as $\Delta n \cdot 2d \leq 100$ nm. As d=0.6 mm, $\Delta n \leq 8.3 \times 10^{-5}$.

As described in "Optics", Vol. 15, No. 5, pp. 414 to 421, the birefringence of the protective layer of an optical recording medium includes in-plane birefringence and perpendicular birefringence. The relationship between the disk 6 as an optical recording medium and the XYZ coordinates is defined as shown in FIG. 2. The X axis, Y axis and Z axis are respectively the radial direction, the tangential direction and the normal direction of the disk 6. The protective layer of the optical recording medium normally has biaxial anisotropy and its three principal axes approximately match with the X axis, Y axis and Z axis. Given that their associated three principal indexes of refraction are nx, ny and nz, respectively, and the in-plane birefringence and perpendicular birefringence are $\Delta n\|$ and $\Delta n\perp$, respectively, the in-plane birefringence is defined as $\Delta n\|=|nx-ny|$ and the perpendicular birefringence as $\Delta n\perp=|(nx+ny)/2-nz|$.

The in-plane birefringence and perpendicular birefringence both reduce the amount of received light at the photosensor which receives reflected light from the optical recording medium and lower the peak intensity of the focused spot to be formed on the optical recording medium. However, the degree of influence on the light which passes through the protective layer of the optical recording medium differs between the in-plane birefringence and perpendicular birefringence. While the influence of the in-plane birefringence does not depend on the incident angle, the influence of the perpendicular birefringence does, and the light with an incident angle of 0° is not influenced but the influence gets greater as the incident angle increases.

In the method of measuring the birefringence characteristic of the protective layer of the conventional optical recording medium described above referring to FIG. 1, the incident angle of to the disk 6 is as small as 7° so that the reflected light from the disk 6 is influenced by the in-plane birefringence but is hardly influenced by the perpendicular birefringence. Therefore, the in-plane birefringence is the only birefringence that is measured by this measuring method. The allowance for birefringence that is determined based on this measuring method is the allowance for the in-plane birefringence and the allowance for the perpendicular birefringence is not determined. In case where recording and playback of an optical recording medium whose protective layer has a thickness of 0.6 mm are carried out using the optical information recording/reproducing apparatus whose light source has a wavelength of 412 nm and whose objective lens has a numerical aperture (NA) of 0.6, if either one of the in-plane birefringence and the perpendicular birefringence of the protective layer of the optical recording medium is greater than the allowance, the amount of received light and the peak intensity decrease, so that the recording density of 8.2 Gbits/inch$^2$ (the recording capacity of 11.7 GBytes) cannot be achieved.

To suppress reduction in the amount of received light and the peak intensity and achieve the recording density of 8.2 Gbits/inch$^2$ while using the optical information recording/reproducing apparatus whose light source has a wavelength of 412 nm and whose objective lens has a numerical aperture (NA) of 0.6, it is necessary to separately measure the in-plane birefringence and perpendicular birefringence in the birefringence characteristic of the protective layer of the optical recording medium, and set the allowance for the birefringence characteristic separately for the in-plane birefringence and perpendicular birefringence In addition, the optical recording medium should have a good protective layer whose birefringence characteristic satisfies the allowances for both the in-plane birefringence and the perpendicular birefringence and which has an excellent recording/playback characteristic.

As a birefringence characteristic measuring method, the incident angle to the disk 6 in the conventional measuring method may be set greater than 7°. If the incident angle to the disk 6 is increased, however, a large phase difference arises on the reflection film between two orthogonal polarized light components, making it impossible to distinguish the birefringence-originated phase difference from the phase difference on the reflection film. Apparently, this method cannot measure the birefringence accurately. Another feasible measuring method is to use a protective layer before deposition of a reflection film instead of the disk 6 in the conventional measuring method, set the incident angle to the protective layer greater than 7° and measure the ellipticity of the elliptically polarized light transmitted through the protective layer instead of the ellipticity of the elliptically polarized light reflected at the disk 6. As the deposition of the reflection film causes the birefringence of the protective layer to vary depending on the stress or the like of the reflection film, however, this method does not accurately measure the birefringence of the protective layer of the disk 6.

SUMMARY OF THE INVENTION

Accordingly, it is an object of the invention to overcome the problems of the conventional methods of measuring the birefringence characteristic of the protective layer of an optical recording medium and provide a birefringence characteristic measuring method which can separately measure the in-plane birefringence and perpendicular birefringence in the birefringence characteristic of the protective layer of an optical recording medium, an optical recording medium which has a protective layer with an excellent birefringence characteristic and has an excellent recording/playback characteristic and an optical information recording/reproducing apparatus using the optical recording medium in order to record and play back high-definition moving pictures for 120 minutes.

To achieve the object, a birefringence characteristic measuring method according to the first aspect of the invention comprises the steps of irradiating light onto a target medium for measurement via an objective lens having a numerical aperture equal to or higher than a predetermined numerical aperture, and measuring an amount of light of a polarized light component in a specific direction, which is included in reflected light reflected at a reflection surface of the target medium to thereby acquire a first amount of light $A_{PH}$; irradiating light onto the target medium via the objective lens having the numerical aperture equal to or higher than the predetermined numerical aperture, and measuring an amount of light of a polarized light component in the specific direction, which is included in reflected light reflected at the reflection surface of the target medium, and an amount of light of a polarized light component in a direction orthogonal to the specific direction to thereby acquire a second amount of light $A_{NH}$; and acquiring a perpendicular birefringence characteristic of the target medium based on a ratio $A_{PH}/A_{NH}$ of the first amount of light to the second amount of light and an in-plane birefringence characteristic of the target medium.

According to the birefringence characteristic measuring method of the first aspect of the invention, the first amount of light and the second amount of light can be measured by guiding reflected light from the target medium to the photosensor via, for example, a polarization optical system and non-polarization optical system Based on the ratio of the first amount of light to the second amount of light, therefore, the perpendicular birefringence characteristic of the target medium can be acquired.

A value selected for the predetermined numerical aperture is such that with the numerical aperture below that value, a reduction in the amount of received light influenced by the perpendicular birefringence in the polarization optical system is substantially negligible and when the numerical aperture is equal to or higher than the value, the reduction in the amount of received light influenced by the perpendicular birefringence rapidly increases with an increase in numerical aperture. For example, 0.4 is selected for the predetermined numerical aperture. A numerical aperture equal to or higher than the predetermined numerical aperture is, for example, 0.5 or higher, and preferably is 0.6 or higher.

In the measuring method according to a preferable mode, light is irradiated onto the target medium via an objective lens having a numerical aperture lower than the predetermined numerical aperture, and reflected light reflected at the reflection surface of the target medium is irradiated on a photosensor via a polarization optical system, and the amount of light of a polarized light component in a specific direction, which is included in reflected light is measured to thereby acquire a third amount of light $A_{PL}$, light is irradiated onto the target medium via the objective lens having the numerical, aperture lower than the predetermined numerical aperture, reflected light reflected at the reflection surface of the target medium is irradiated on the photosensor via a non-polarization optical system, and the amount of light of a polarized light component in the specific direction, which is included in the reflected light and the amount of light of a polarized light component in a direction orthogonal to the specific direction are measured to thereby acquire a fourth amount of light $A_{NL}$, and the in-plane birefringence characteristic is acquired based on a ratio $A_{PL}/A_{NL}$ of the third amount of light to the fourth amount of light. As the in-plane birefringence can be measured by merely changing the objective lens of each optical system, the birefringence characteristic is obtained easily. For example, 0.3 is selected for a numerical aperture (NA) lower than the predetermined numerical aperture.

According to another preferable mode of the invention, the optical system that is used at the time of measuring the first amount of light is constructed by a polarization optical system which outputs a polarized light component in the specific direction in the incident reflected light, and the optical system that is used at the time of measuring the second amount of light is constructed by a non-polarization optical system which outputs a polarized light component in the specific direction in the incident reflected light and a polarized light component in a direction orthogonal to the specific direction at an approximately same ratio. For example, the ratio can be set to 50%.

According to a further preferable mode of the invention, first to fourth amounts of light for normalization $B_{PH}$, $B_{NH}$, $B_{PL}$ and $B_{NL}$ respectively corresponding to the first to fourth amounts of light are measured using a reference medium which does not substantially have birefringence in place of the target medium, and the first to fourth amounts of light $A_{PH}$, $A_{NH}$, $A_{PL}$ and $A_{NL}$ are respectively normalized based on the first to fourth amounts of light for normalization. Because the utilization factor of light differs between a polarization optical system and a non-polarization optical system, the execution of such normalization can provide a more accurate birefringence characteristic.

A birefringence characteristic measuring method according to the second aspect of the invention measures a birefringence characteristic of a protective layer of an optical recording medium using a birefringence characteristic measuring apparatus having a light source, a photosensor, and an optical system which includes a beam splitter, a quarter-wave plate for passing light output from the light source and passed through the beam splitter and an objective lens for irradiating the light, transmitted through the quarter-wave plate, onto a target optical recording medium for measurement and which guides reflected light reflected from the target optical recording medium to the photosensor via the objective lens, the quarter-wave plate and the beam splitter, and is characterized in that the optical system is switched among a first optical system which guides only a polarized light component in a specific direction in the reflected light reflected from the target optical recording medium using an objective lens having a numerical aperture equal to or higher than a predetermined numerical aperture, a second optical system which guides only a polarized light component in the specific direction in the reflected light reflected from the target optical recording medium using an objective lens having a numerical aperture lower than the predetermined numerical aperture, a third optical system which guides a polarized light component in the specific direction and a polarized light component in a direction orthogonal to the specific direction, both included in the reflected light reflected from the target optical recording medium, at an approximately same ratio, using an objective lens having a numerical aperture equal to or higher than the predetermined numerical aperture, and a fourth optical system which guides a polarized light component in the specific direction and a polarized light component in a direction orthogonal to the specific direction, both included in the reflected light reflected from the target optical recording medium, at an approximately same ratio, using an objective lens having a numerical aperture lower than the predetermined numerical aperture.

The in-plane birefringence characteristic and perpendicular birefringence characteristic both can be acquired effectively by measuring the amount of light of a polarized light component in a specific direction and the amounts of lights of polarized light components in a specific direction and a direction orthogonal to the specific direction using the first to fourth optical systems. The first to fourth optical systems may be constructed separately or with common parts used, only a specific part may be changed as needed.

In the birefringence characteristic measuring method according to the second aspect of the invention, it is preferable that based on amounts of received light measured for a reference optical recording medium having a protective layer which does not substantially have birefringence, using the first to fourth optical systems, amounts of received light measured for the target optical recording medium using the first to fourth optical systems should be normalized respectively.

Given that the amounts of received light measured for the target optical recording medium by the first to fourth optical systems are respectively $A_{PH}$, $A_{PL}$, $A_{NH}$ and $A_{NL}$ and the amounts of received light measured for the reference optical recording medium by the first to fourth optical systems are respectively $B_{PH}$, $B_{PL}$, $B_{NH}$ and $B_{NL}$, an in-plane birefringence characteristic and a perpendicular birefringence characteristic of the target optical recording medium can be acquired respectively from $$L\| = (A_{PL}/B_{PL})/(A_{NL}/B_{NL}), \text{ and}$$

$$L\bot = [(A_{PH}/B_{PH})/(A_{NH}/B_{NH})]/[(A_{PL}/B_{NL})/(A_{NL}/B_{NL})].$$

As $L\|$ and $L\bot$ respectively represent the relative amount of received light including the influence of only the in-plane birefringence and the relative amount of received light including the influence of only the perpendicular birefringence, with the amount of received light in case of no birefringence present taken as a reference, the in-plane birefringence characteristic and the perpendicular birefringence characteristic can be acquired separately.

In the birefringence characteristic measuring method according to the second aspect of the invention, if the protective layer of the optical recording medium has birefringence, the amounts of received lights in the first and second optical systems decrease while the amounts of received lights in the third and fourth optical systems do not. Therefore, the relative amount of received light in case where there is birefringence, with the amount of received light in case of no birefringence present taken as a reference, can be acquired from the ratio of the amounts of received lights in the first and second optical systems to the amounts of received lights in the third and fourth optical systems. In each optical system, if the amount of received light with respect to a target optical recording medium for measurement is normalized by the amount of received light with respect to the reference optical recording medium, a difference in the utilization factor of light from the optical recording medium to the photosensor can be canceled out. In case of the second optical system whose objective lens has a low numerical aperture, while the amount of received light is reduced by the influence of the in-plane birefringence, a reduction in the amount of received light by the influence of the perpendicular birefringence is negligible. In case of the first optical system whose objective lens has a high numerical aperture, a reduction in the amount of received light by the influence of the in-plane birefringence and a reduction in the amount of received light by the influence of the perpendicular birefringence both occur. Accordingly, L∥ and L⊥ respectively represent the relative amount of received light including the influence of only the in-plane birefringence and the relative amount of received light including the influence of only the perpendicular birefringence, with the amount of received light in case of no birefringence present taken as a reference. Therefore, the in-plane birefringence and perpendicular birefringence in the birefringence characteristic of the protective layer of the optical recording medium can be measured separately by measuring L∥ and L⊥.

An optical recording medium according to the first aspect of the invention is an optical recording medium whose recording or playback is carried out at a recording density of 8.2 Gbits/inch$^2$ or higher using an optical information recording/reproducing apparatus having a light source with a wavelength of 412 nm or less and an objective lens with a numerical aperture of 0.6 or higher, and is characterized by having a protective layer with a thickness of about 0.6 mm through which light is transmitted and whose L∥ obtained as L∥=$(A_{PL}/B_{PL})/(A_{NL}/B_{NL})$ is L∥≧0.79.

An optical recording medium according to the second aspect of the invention is an optical recording medium whose recording or playback is carried out at a recording density of 8.2 Gbits/inch$^2$ or higher using an optical information recording/reproducing apparatus having a light source with a wavelength of 412 nm or less and an objective lens with a numerical aperture of 0.6 or higher and is characterized by having a protective layer with a thickness of about 0.6 mm through which light is transmitted and in which $\Delta n\| \cdot 2d \leq 64$ nm where $\Delta n\|$ is a value of in-plane birefringence of the protective layer and d is a thickness of the protective layer.

An optical recording medium according to the third aspect of the invention is an optical recording medium whose recording or playback is carried out at a recording density of 8.2 Gbits/inch$^2$ or higher using an optical information recording/reproducing apparatus having a light source with a wavelength of 412 nm or less and an objective lens with a numerical aperture of 0.6 or higher, and is characterized by having a protective layer with a thickness of about 0.6 mm through which light is transmitted and whose L⊥ obtained as L⊥= $(A_{PH}/B_{PH})/(A_{NH}/B_{NH})]/[(A_{PL}/B_{PL})/(A_{NL}/B_{NL})]$ is L⊥≧0.57. Alternatively, this $(A_{PL}/B_{PL})/(A_{NL}/B_{NL})$ can be acquired by separately measuring the value of the in-plane birefringence of the protective layer and converting the value to L∥.

An optical information recording/reproducing apparatus according to the first aspect of the invention has a light source with a wavelength of 412 nm or less and an objective lens with a numerical aperture of 0.6 or higher and records or plays back, at a recording density of 8.2 Gbits/inch$^2$ or higher, an optical recording medium which has a protective layer with a thickness of about 0.6 mm through which light is transmitted and whose L∥ acquired as L∥=$(A_{PL}/B_{PL})/(A_{NL}/B_{NL})$ is L∥≧0.79.

An optical information recording/reproducing apparatus according to the second aspect of the invention has a Light source with a wavelength of 412 nm or less and an objective lens with a numerical aperture of 0.6 or higher and records or plays back, at a recording density of 8.2 Gbits/inch$^2$ or higher, an optical recording medium which has a protective layer with a thickness of about 0.6 mm through which light is transmitted and in which $\Delta n\| \cdot 2d \leq 64$ nm where $\Delta n\|$ is a value of in-plane birefringence of the protective layer and d is the thickness of the protective layer.

An optical information recording/reproducing apparatus according to the third aspect of the invention has a light source with a wavelength of 412 nm or less and an objective lens with a numerical aperture of 0.6 or higher and records or plays back, at a recording density of 8.2 Gbits/inch$^2$ or higher, an optical recording medium which has a protective layer with a thickness of about 0.6 mm through which light is transmitted and whose L⊥ acquired as L⊥=$[(A_{PH}/B_{PH})/(A_{NH}/B_{NH})]/[(A_{PL}/B_{PL})/(A_{NL}/B_{NL})]$ is L⊥≧0.57. Alternatively, this $(A_{PL}/B_{PL})/(A_{NL}/B_{NL})$ can be acquired by separately measuring the value of the in-plane birefringence of the protective layer and converting the value to L∥.

In the optical recording medium according to the invention and the optical information recording/reproducing apparatus using that optical recording medium, L∥≧0.79 and $\Delta n\| \cdot 2d \leq 64$ nm are equivalent to the case where the amount of received light at the photosensor with the in-plane birefringence present is equal to or greater than the allowance for the amount of light based on the allowance for birefringence of DVDs L⊥≧0.57 is equivalent to the case where the peak intensity of the focused spot with the perpendicular birefringence present is equal to or greater than the allowance for of the peak intensity based on the Marechal's criterion concerning wavefront aberration. When the wavelength of the light source is 412 nm or shorter, the numerical aperture of the objective lens is 0.6 or higher and the thickness of the protective layer of the optical recording medium is 0.6 mm, therefore, it is possible to achieve the recording density of 8.2 Gbits/inch$^2$ or higher which is equivalent to the square of the wavelength ratio according to the DVD specifications and is needed to record and play back high-definition moving pictures for 120 minutes.

In short, the invention can realize the birefringence characteristic measuring method capable of separately measuring the in-plane birefringence and perpendicular birefringence in the birefringence characteristic of the protective layer of an optical recording medium, and an optical recording medium which has a protective layer with an excellent birefringence characteristic and has an excellent recording/playback characteristic, and an optical information recording/reproducing apparatus using that optical recording medium in order to record and play back high-definition moving pictures for 120 minutes.

In other words, the birefringence characteristic measuring method according to the invention can measure the perpendicular birefringence of a target medium for measurement separately from the in-plane birefringence of the target medium, so that the method, if adapted to the protective layer of an optical recording medium, for example, can easily acquire the birefringence characteristic of the protective layer of the optical recording medium and can be utilized in manufacture and design of an optical recording medium and an optical information recording/reproducing apparatus.

According to the optical recording medium embodying the invention and the optical information recording/reproducing apparatus which uses this optical recording medium, the birefringence characteristic of the protective layer of the optical recording medium satisfies the allowances for both the in-plane birefringence and perpendicular birefringence and the recording density of 8.2 Gbits/inch$^2$ or higher is achieved, thus ensuring recording and playback of high-definition moving pictures for 120 minutes.

DETAILED DESCRIPTION OF THE PREFERRED EMBODIMENTS

Figure 1:
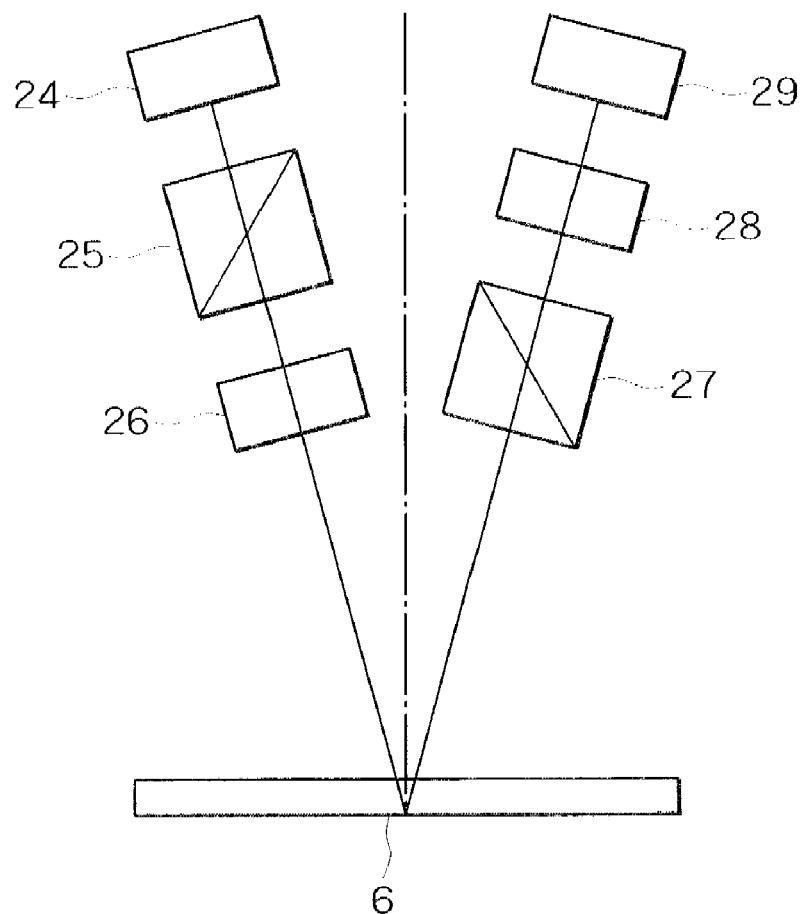
FIG. 1 is a diagram showing a conventional the birefringence characteristic of the protective layer of an optical recording medium.

The invention will be described below based on embodiments of the invention referring to the accompanying drawings. A birefringence characteristic measuring method according to one embodiment of the invention does not measure the birefringence of the protective layer of, for example, an optical recording medium itself, but irradiates output light from a light source onto an optical recording medium via an objective lens and measures the amount of received light at a photosensor when reflected light from the optical recording medium is received via the objective lens at the photosensor. As an optical system including a light source, an objective lens and a photosensor, four kinds are used, which are a polarization optical system whose objective lens has a high numerical aperture (NA), a polarization optical system whose objective lens has a low numerical aperture (NA), a non-polarization optical system whose objective lens has a high numerical aperture (NA) and a non-polarization optical system whose objective lens has a low numerical aperture (NA). Here, the "polarization optical system" is an optical system in which, of light that is the reflected light from an optical recording medium which has passed through a quarter-wave plate, only a polarized light component in a specific direction is received by the photosensor, while the "non-polarization optical system" is an optical system in which, of light that is the reflected light from an optical recording medium which has passed through a quarter-wave plate, a polarized light component in a specific direction and a polarized light component in a direction orthogonal to the specific direction are received by the photosensor at the same ratio. As an optical recording medium, two types are used which is a target disk for measurement the birefringence characteristic of whose protective layer is to be measured and a glass disk whose protective layer is glass that does not have birefringence. The glass disk may be replaced with any other disk whose protective layer is made of a material having no birefringence.

Table 1 below shows combinations of the four types of optical systems and the two types of optical recording media in the method of measuring the birefringence characteristic of the protective layer of an optical recording medium according to the embodiment of the invention.

TABLE 1

|  | Target disk | Glass disk |
|---|---|---|
| Polarization optical system (high NA) | $A_{PH}$ | $B_{PH}$ |
| Polarization optical system (low NA) | $A_{PL}$ | $B_{PL}$ |
| Non-polarization optical system (high NA) | $A_{NH}$ | $B_{NH}$ |
| Non-polarization optical system (low NA) | $A_{NL}$ | $B_{NL}$ |

As shown in Table 1, the amount of received light at the photosensor is measured for each of the total of eight combinations. The amounts of received lights at the photosensor for the individual combinations are given by the corresponding symbols in the Table 1. $L\|$ and $L\perp$ are acquired from those amounts of received lights by the following equations $$L\| = (A_{PL}/B_{PL})/(A_{NL}/B_{NL})$$

$$L\perp = [(A_{PH}/B_{PH})]/[(A_{NH}/B_{NH})]/[(A_{PL}/B_{PL})/(A_{NL}/B_{NL})]$$

Without birefringence in the protective layer of the optical recording medium, reflected light from the optical recording medium which is received at the photosensor has only a polarized light component in the specific direction. With birefringence in the protective layer of the optical recording medium, however, a polarized light component in the specific direction in reflected light from the optical recording medium which is received at the photosensor is reduced while a polarized light component in a direction orthogonal to the specific direction is produced. In case where a polarization optical system is used, only a polarized light component in the specific direction is received at the photosensor, so that if the protective layer of the optical recording medium has birefringence, the amount of received light at the photosensor is reduced. In case where a non-polarization optical system is used, a polarized light component in a specific direction and a polarized light component in a direction orthogonal to the specific direction are received at the photosensor at the same ratio. Even if the protective layer of the optical recording medium has birefringence, therefore, the amount of light received at the photosensor does not change. Therefore, the relative amount of received light in case where there is birefringence, with the amount of received light in case of no birefringence present taken as a reference, can be acquired from the ratio of the amounts of received lights in the polarization optical system and the non-polarization optical system. Because the utilization factor of light from the optical recording medium to the photosensor differs between the polarization optical system and the non-polarization optical system, it is preferable that the amount of received light in each optical system should be normalized by the amount of received light with respect to the glass disk whose protective layer does not have birefringence.

While the influence of the in-plane birefringence does not depend on the incident angle, the influence of the perpendicular birefringence does, and the light with an incident angle of 0° is not influenced but the influence gets greater as the incident angle increases. In case of a polarization optical system whose objective lens has a low numerical aperture (NA), the incident angle to the optical recording medium is small so that the in-plane birefringence decreases the amount of received light while a reduction in the amount of received light caused by the perpendicular birefringence is small. If the numerical aperture (NA) of the objective lens is sufficiently low, a reduction in the amount of received light caused by the perpendicular birefringence can be neglected. In case of a polarization optical system whose objective lens has a high numerical aperture (NA), by way of contrast, the incident angle to the optical recording medium is small in the center portion of the objective lens but is large around the objective lens. This causes both a reduction in the amount of received light originated from the influence of the in-plane birefringence and a reduction in the amount of received light originated from the influence of the perpendicular birefringence.

As apparent from the above, $(A_{PL}/B_{PL})/(A_{NL}/B_{NL})$ or $L\|$ represents the relative amount of received light including the influence of only the in-plane birefringence with the amount of received light in case of no birefringence present as a reference, whereas $(A_{PH}/B_{PH})/(A_{NH}/B_{NH})$ represents the relative amount of received light including both the influences of the in-plane birefringence and perpendicular birefringence with the amount of received light in case of no birefringence present as a reference. Because the latter expression is the product of the former expression and the relative amount of received light including the influence of only the perpendicular birefringence, the relative amount of received light including the influence of only the perpendicular birefringence is expressed by $[(A_{PH}/B_{PH})/(A_{NH}/B_{NH})]/[(A_{PL}/B_{PL})/(A_{NL}/B_{NL})]$ or $L\perp$. Therefore, measuring $L\|$ and $L\perp$ is to separately measure the in-plane birefringence and perpendicular birefringence in the birefringence characteristic of the protective layer of the optical recording medium.

With regard to in-plane birefringence, a method of measuring the birefringence characteristic of the protective layer of an optical recoding medium according to another embodiment of the invention measures the birefringence itself. With regard to perpendicular birefringence, on the other hand, this measuring method irradiates output light from the light source to an optical recording medium via the objective lens and measures the amount of received light at the photosensor upon reception of reflected light from the optical recording medium via the objective lens. First, the in-plane birefringence is measured by the method that has been described earlier referring to FIG. 1. As will be discussed later, the relationship between the in-plane birefringence $\Delta n\|$ and the relative amount of received light including the influence of only the in-plane birefringence is acquired by computation, so that the measured $\Delta n\|$ can be converted to $L\|$. Next, the amounts of received lights $A_{PH}$, $B_{PH}$, $A_{NH}$ and $B_{NH}$ are measured using a polarization optical system whose objective lens has a high numerical aperture (NA) and a non-polarization optical system whose objective lens has a high numerical aperture (NA). The relative amount of received light $L\perp$ including the influence of only the perpendicular birefringence is acquired from $L\|$ and those amounts of received lights by the following equation $$L\perp = [(A_{PH}/B_{PH})/(A_{NH}/B_{NH})]/L\|$$

In the embodiment, it is unnecessary to use a polarization optical system whose objective lens has a low numerical aperture (NA) and non-polarization optical system whose objective lens has a low numerical aperture (NA).

Figure 3:
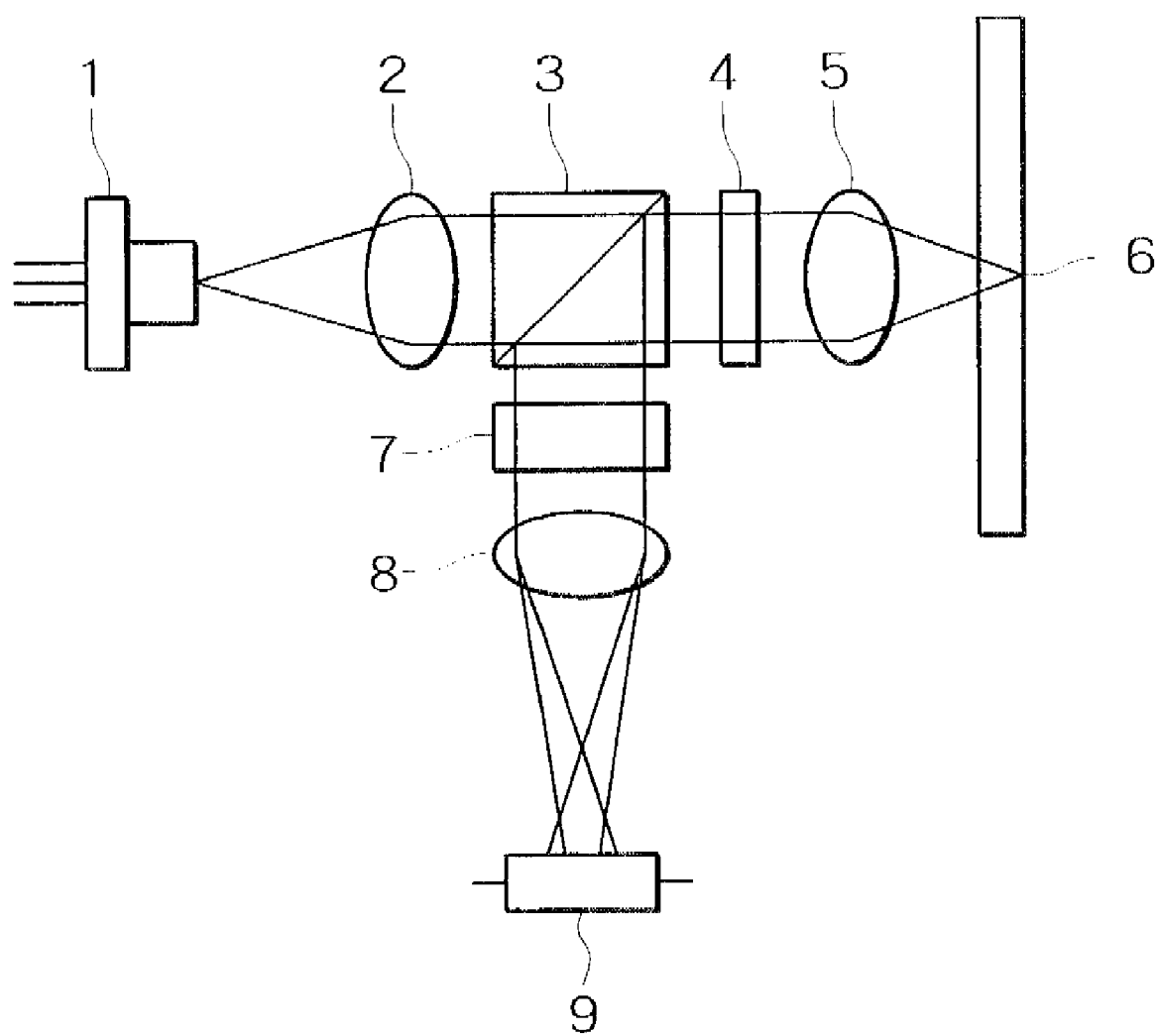
FIG. 3 is a diagram illustrating the structure of a polarization optical system to be used in a method of measuring the birefringence characteristic of the protective layer of an optical recording medium according to one embodiment of the invention.

FIG. 3 is a diagram illustrating the structure of a polarization optical system. A polarization beam splitter 3 works to almost completely pass a P-polarized light component in input light but almost completely reflect an S-polarized light component. The output light from a semiconductor laser 1 is converted by a collimator lens 2 to parallel light which is input as P-polarized light to the polarization beam splitter 3 and nearly completely passes through it. The light then passes a quarter-wave plate 4 to be converted from linearly polarized light to circularly polarized light which is focused on a disk 6 by an objective lens 5. The disk 6 is a target disk for measurement or a glass disk. In case where the protective layer of the disk 6 does not have birefringence, reflected light from the disk 6 passes through an objective lens 5 in the reverse direction and passes through the quarter-wave plate 4 to be converted from circularly polarized light to linearly polarized light whose polarization direction is orthogonal to the forward path. Next, the Linearly polarized light enters the polarization beam splitter 3 as S-polarized light and is nearly completely reflected, further passes through a cylindrical lens 7 and a lens 8 to be received at a photosensor 9. The photosensor 9 is located in a middle between two focal lines of the cylindrical lens 7 and lens 8.

In case where the protective layer of the disk 6 has birefringence, reflected light from the disk 6 passes through the quarter-wave plate 4 to be converted to elliptically polarized light. While the S-polarized light component is almost completely reflected at the polarization beam splitter 3 and is received at the photosensor 9, the P-polarized light component nearly completely passes through the polarization beam splitter 3 and returns to the semiconductor laser 1. That is, in this optical system, of the reflected light from the disk 6, only the S-polarized light component with respect to the polarization beam splitter 3 is received at the photosensor 9.

The numerical aperture (NA) of the objective lens 5 is set to the same value (e.g., 0.6) as the numerical aperture of the objective lens in an optical information recording/reproducing apparatus which actually performs recording and playback on a target disk for measure in case of a high numerical aperture (equal to or higher than a predetermined numerical aperture), but is set to a sufficiently low value (e.g., 0.3) such that a reduction in the amount of received light caused by the influence of perpendicular birefringence in the polarization optical system is negligible in case of a low numerical aperture (less than the predetermined numerical aperture). At this time, instead of using the objective lens 5 with a low numerical aperture, an objective lens having a high numerical aperture may be used as the objective lens 5 with an unillustrated aperture restricting element having an aperture smaller in diameter than the effective diameter of the objective lens 5 inserted between the quarter-wave plate 4 and the objective lens 5, thereby lowering the effective numerical aperture of the objective lens 5. The wavelength of the semiconductor laser 1 is set to the same value (e.g., 412 nm) as the wavelength of the light source in the optical information recording/reproducing apparatus which actually performs recording and playback on a target disk for measure.

Figure 4:
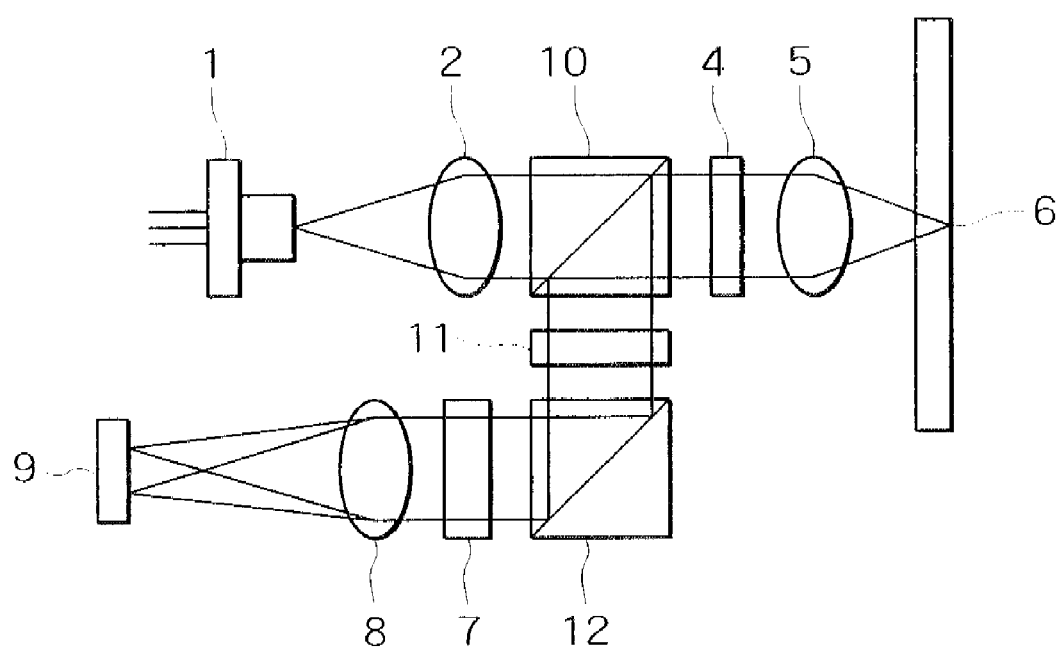
FIG. 4 is a diagram illustrating the structure of a non-polarization optical system to be used in the method of measuring the birefringence characteristic of the protective layer of the optical recording medium according to the embodiment of the invention.

FIG. 4 is a diagram illustrating the structure of a non-polarization optical system. Partial polarization beam splitters 10 and 12 work to pass about 50% of a P-polarized light component in input light and reflect about 50% of the P-polarized light component, and almost completely reflect an S-polarized light component. The output light from a semiconductor laser 1 is converted by the collimator lens 2 to parallel light which is input as P-polarized light to the partial polarization beam splitter 10. About 50% of the P-polarized light component passes through the beam splitter 10, passes the quarter-wave plate 4 to be converted from linearly polarized light to circularly polarized light which is focused on the disk 6 by an objective lens 5. The disk 6 is a target disk for measurement or a glass disk. In case where the protective layer of the disk 6 does not have birefringence, reflected light from the disk 6 passes through the objective lens 5 in the reverse direction and passes through the quarter-wave plate 4 to be converted from circularly polarized light to linearly polarized light whose polarization direction is orthogonal to the forward path. Next, the linearly polarized light enters the partial polarization beam splitter 10 as S-polarized light and is nearly completely reflected, further passes through a half-wave plate 11 so that its polarization direction changes by 90°. The light then enters the partial polarization beam splitter 12 as P-polarized light about 50% of which is reflected and further passes through the cylindrical lens 7 and lens 8 to be received at the photosensor 9. The photosensor 9 is located in a middle between two focal lines of the cylindrical lens 7 and lens 8.

In case where the protective layer of the disk 6 has birefringence, reflected light from the disk 6 passes through the quarter-wave plate 4 to be converted to elliptically polarized light. The S-polarized light component is almost completely reflected at the partial polarization beam splitter 10 and passes through the half-wave plate 11, changing its polarization direction by 90°. The light then enters the partial polarization beam splitter 12 as P-polarized light about 50% of which is reflected and received at the photosensor 9. On the other hand, about 50% of the P-polarized light component is reflected at the partial polarization beam splitter 10 and passes through the half-wave plate 11, changing its polarization direction by 90°. The light then enters the partial polarization beam splitter 12 as S-polarized light and is almost completely reflected and received at the photosensor 9. That is, in this optical system, of the reflected light from the disk 6, the S-polarized light component and P-polarized light component with respect to the partial polarization beam splitter 10 are received at the photosensor 9 each by a ratio of 50%.

The numerical aperture (NA) of the objective lens 5 is set to the same value (e.g., 0.6) as the numerical aperture of the objective lens in an optical information recording/reproducing apparatus which actually performs recording and playback on a target disk for measure in case of a high numerical aperture (equal to or higher than a predetermined numerical aperture), but is set to a sufficiently low value (e.g., 0.3) such that a reduction in the amount of received light caused by the influence of perpendicular birefringence in the polarization optical system is negligible in case of a low numerical aperture (less than the predetermined numerical aperture). At this time, instead of using the objective lens 5 with a low numerical aperture, an objective lens having a high numerical aperture may be used as the objective lens 5 with an unillustrated aperture restricting element having an aperture smaller in diameter than the effective diameter of the objective lens 5 inserted between the quarter-wave plate 4 and the objective lens 5, thereby lowering the effective numerical aperture of the objective lens 5. The wavelength of the semiconductor laser 1 is set to the same value (e.g., 412 nm) as the wavelength of the light source in the optical information recording/reproducing apparatus which actually performs recording and playback on a target disk for measure.

Figure 5:
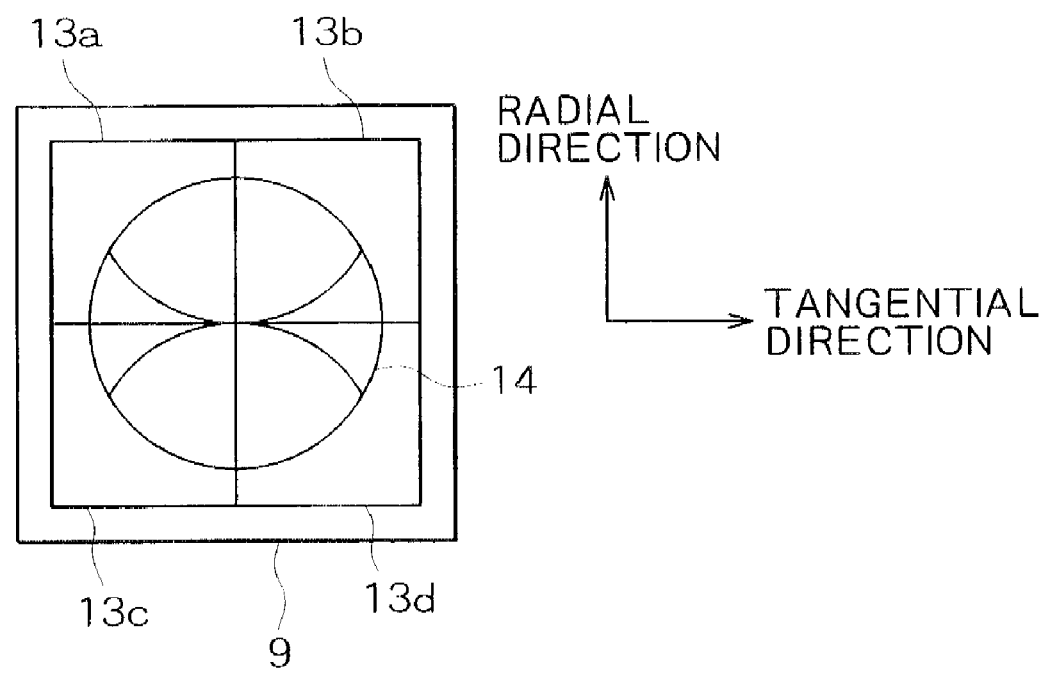
FIG. 5 is a diagram illustrating the structure of a photosensor to be used in the method of measuring the birefringence characteristic of the protective layer of the optical recording medium according to the embodiment of the invention.

In case of a high numerical aperture (equal to or higher than a predetermined numerical aperture), the numerical aperture (NA) of the objective lens 5 is set to the same value as the numerical aperture of the objective lens in the actual optical information recording/reproducing apparatus, and the wavelength of the semiconductor laser 1 is set to the same wavelength as the wavelength of the light source in the actual optical information recording/reproducing apparatus, so that the birefringence characteristic of the protective layer of the optical recording medium can be measured separately as into in-plane birefringence and perpendicular birefringence under the same conditions as the actual optical information recording/reproducing apparatus FIG. 5 is a diagram illustrating the structure of the photosensor 9. The reflected light from the disk 6 forms a light spot 14 on light receiving sections 13a to 13d quadrisected by a dividing line parallel to the radial direction of the disk 6 and a dividing line parallel to the tangential direction. Provided that outputs from the light receiving sections 13a to 13d are given by V13a to V13d, respectively, a focus error signal is acquired from an arithmetic operation of (V13a+V13d)−(V13b+V13c) by an astigmatism method. A track error signal is acquired from a phase difference between (V13a+V13d) and (V13b+V13c) by a differential phase detection method in case where the disk 6 is of a read-only type and is acquired from an arithmetic operation of (V13a+V13b)−(V13c+V13d) by a push-pull method in case where the disk 6 is of a recordable type or re-recordable type. A sum signal equivalent to the amount of received light at the photosensor 9 is acquired from an arithmetic operation of (V13a+V13b+V13c+V13d). The amount of received light at the photosensor 9 is measured as a focus servo and/or track servo is applied as needed.

Figure 2:
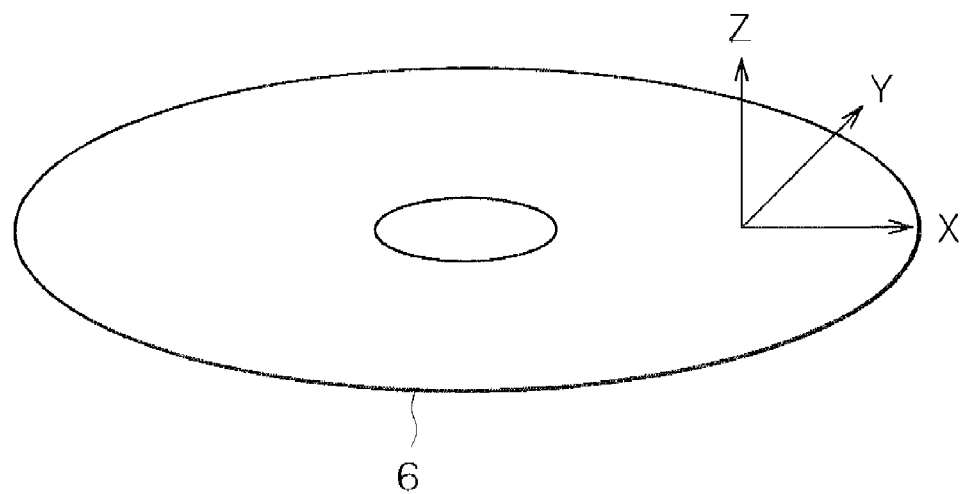
FIG. 2 is a diagram showing the relationship between an optical recording medium and the XYZ coordinates.

A description will now be given of the relationship among the in-plane birefringence and perpendicular birefringence in a polarization optical system and the amount of received light and the peak intensity. With the X axis and Y axis defined in a cross section perpendicular to the optical axis, as shown in FIG. 2, the P-polarized light component and S-polarized light component with respect to the polarization beam splitter 3 are expressed by using a Jones vector. Provided that the electric field distribution of the output light from the semiconductor laser 1 is $E_0(x,y)$ and the Jones matrix of the quarter-wave plate 4 is Q and the Jones matrix of the protective layer of the disk 6 is S, the Jones vector of the light which has come out of the polarization beam splitter 3 and has passed through the quarter-wave plate 4 and the protective layer of the disk 6 in the forward path to the disk 6 from the semiconductor laser 1 is given by the following equation.

$$\begin{pmatrix} E_{p0}(x, y) \\ E_{s0}(x, y) \end{pmatrix} = S \cdot Q \cdot \begin{pmatrix} E_0(x, y) \\ 0 \end{pmatrix} \qquad \text{Eq. 1}$$

The Jones vector of the light which has passed through the protective layer of the disk 6 and the quarter-wave plate 4 and has entered the polarization beam splitter 3 in the return path to the photosensor 9 from the disk 6 is given by the following equation.

$$\begin{pmatrix} E_p(x, y) \\ E_s(x, y) \end{pmatrix} = Q^* \cdot S^* \cdot \begin{pmatrix} E_{p0}^*(-x, -y) \\ E_{s0}^*(-x, -y) \end{pmatrix} \qquad \text{Eq. 2}$$

Q and S are given by the following equations.

$$Q = \frac{1}{\sqrt{2}} \begin{pmatrix} 1 & -i \\ -i & 1 \end{pmatrix} \qquad \text{Eq. 3}$$

$$S = \begin{pmatrix} A & B \\ B & C \end{pmatrix}$$

$$A = \cos\frac{\alpha}{2} + i\cos 2(\theta + \varphi)\sin\frac{\alpha}{2}$$

$$B = i\sin 2(\theta + \varphi)\sin\frac{\alpha}{2}$$

$$C = \cos\frac{\alpha}{2} - i\cos 2(\theta + \varphi)\sin\frac{\alpha}{2}$$

$$\varphi = \tan^{-1}\frac{y}{x}$$

Considering an ellipse which is a cross section perpendicular to the light beam of an index ellipsoid on the protective layer of the disk 6, α is the birefringence-originated phase difference between a polarized light component in the direction of the long axis of the ellipse and a polarized light component in the direction of the short axis and θ is an angle representing the direction of the long axis of the ellipse or the direction of the short axis. How to obtain α and θ is described in "Optics", Vol. 15, No. 5, pp. 414 to 421.

Let L be the amount of received light at the photosensor 9. Then, L is given by the following equation.

$$L \propto \iint |E_s(x,y)|^2 dx dy \qquad \text{Eq. 4}$$

Let P be the peak intensity of the focused spot. Then, P is given by the following equation.

$$P \propto |\iint E_{p0}(x,y)dxdy|^2 + |\iint E_{s0}(x,y)dxdy|^2 \qquad \text{Eq. 5}$$

As the Jones matrix S of the protective layer of the disk 6 is a function of the in-plane birefringence $\Delta n\|$ and the perpendicular birefringence $\Delta n\perp$, L and P are also functions of $\Delta n\|$ and $\Delta n\perp$.

Figure 6:
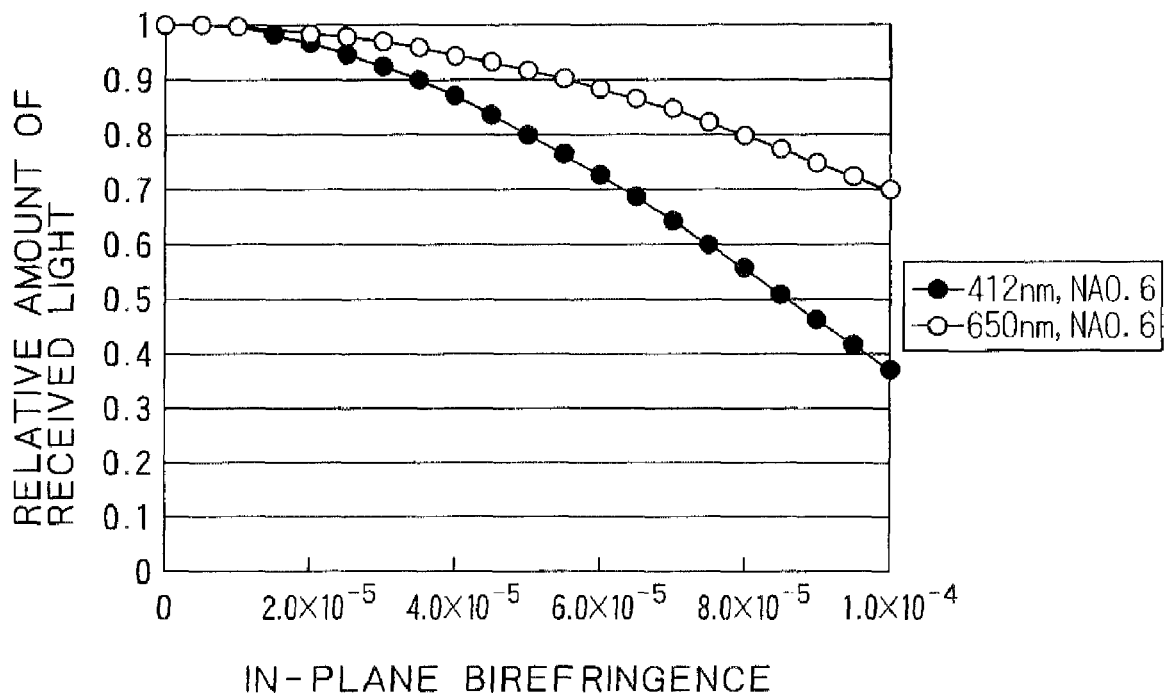
FIG. 6 is a diagram showing an example of computation of the relationship between in-plane birefringence and the relative amount of received light.

FIG. 6 shows an example of computation of the relationship between in-plane birefringence and the relative amount of received light. The horizontal axis in FIG. 6 indicates the in-plane birefringence $\Delta n\|$ and the vertical axis is the relative amount of received light ($L\|$) obtained by normalizing the amount of received light L in case where only in-plane birefringence is present by the amount of received light in case of no birefringence present. The calculation conditions indicated by black circles are the wavelength of the light source being 412 nm and the numerical aperture (NA) of the objective lens being 0.6, which are equivalent to those of the embodiment of the optical information recording/reproducing apparatus according to the invention and the calculation conditions indicated by white circles are the wavelength of the light source being 650 nm, the numerical aperture (NA) of the objective lens being 0.6, which are equivalent to the DVD specifications. The thickness of the protective layer of the optical recording medium being 0.6 mm. It is apparent that as the in-plane birefringence increases, the relative amount of received light decreases and the shorter the wavelength of the light source is, the greater the degree of the reduction in the relative amount of received light becomes.

Figure 7:
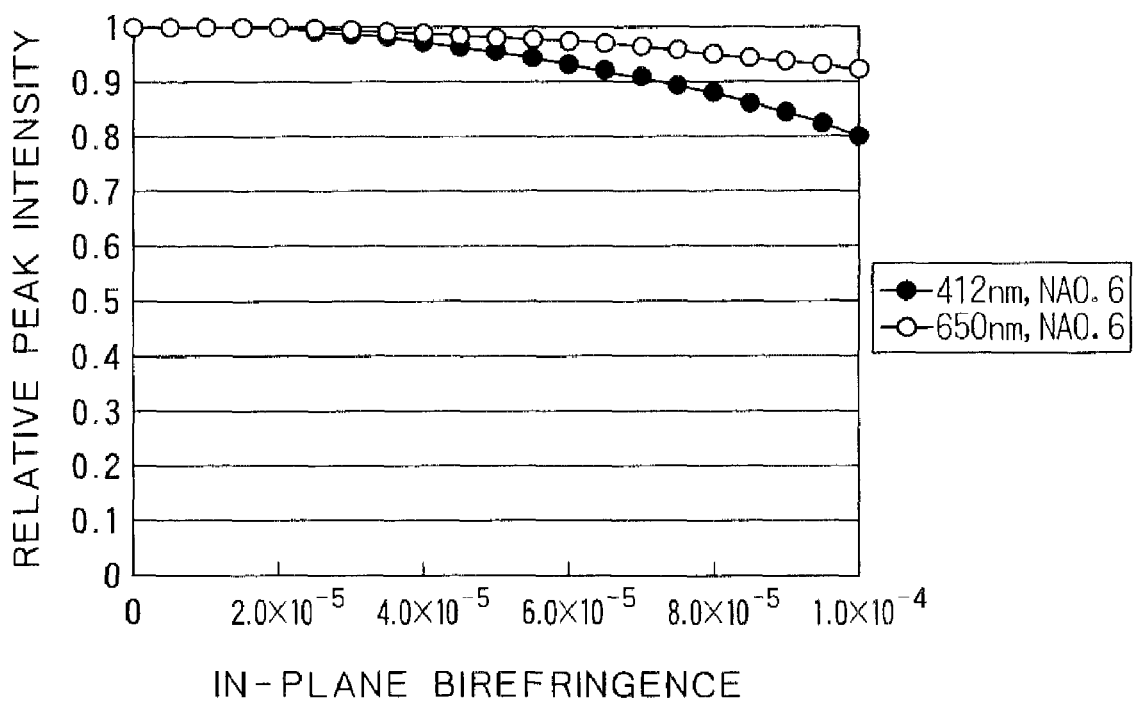
FIG. 7 is a diagram showing an example of computation of the relationship between in-plane birefringence and the relative peak intensity.

FIG. 7 shows an example of computation of the relationship between in-plane birefringence and the relative peak intensity. The horizontal axis in FIG. 7 indicates the in-plane birefringence $\Delta n\|$ and the vertical axis is the relative peak intensity obtained by normalizing the peak intensity P in case where only in-plane birefringence is present by the peak intensity in case of no birefringence present. The calculation conditions indicated by black circles are the wavelength of the light source being 412 mm and the numerical aperture (NA) of the objective lens being 0.6, which are equivalent to those of the embodiment of the optical information recording/reproducing apparatus according to the invention and the calculation conditions indicated by white circles are the wavelength of the light source being 650 nm, the numerical aperture (NA) of the objective lens being 0.6, which are equivalent to the DVD specifications. The thickness of the protective layer of the optical recording medium being 0.6 mm. It is apparent that as the in-plane birefringence increases, the relative peak intensity decreases and the shorter the wavelength of the light source is, the greater the degree of the reduction in relative peak intensity becomes.

The allowance for birefringence described in the specifications of DVD-ROM, DVD-R and DVD-RW is the allowance for in-plane birefringence and is expressed as $\Delta n\| \leq 8.3 \times 10^{-5}$ in terms of $\Delta n\|$. This value, when converted to the allowance for the relative amount of received light from FIG. 6, becomes $L\| \geq 0.79$. According to an optical recording medium whose protective layer has a thickness of 0.6 mm and whose recording and playback are carried out by an optical information recording/reproducing apparatus whose light source has a wavelength of 412 nm and whose objective lens has a numerical aperture (NA) of 0.6, the allowance for the relative amount of received light in case where there is in-plane birefringence should at least be the same as that of DVDs in order to achieve the recording density of 8.2 Gbits/inch$^2$ which is equivalent to the square of the wavelength ratio according to the DVD standard. That is, the allowance for the relative amount of received light becomes $L\| \geq 0.79$. This value, when converted to the allowance for in-plane birefringence from FIG. 5, becomes $\Delta n\| \leq 5.3 \times 10^{-5}$ ($\Delta n\| \cdot 2d \leq 64$ nm). The allowance for in-plane birefringence is basically the same for the case where the wavelength of the light source is set to 412 nm or shorter and the numerical aperture (NA) of the objective lens is set to 0.6 or higher to increase the recording density accordingly to 8.2 Gbits/inch$^2$ or greater. In the optical recording medium according to the embodiment of the invention, as the relative amount of received light satisfies this allowance and is $L\| \geq 0.79$, it is possible to achieve the recording density of 8.2 Gbits/inch$^2$ necessary to record and play back high-definition moving pictures for 120 minutes.

Figure 8:
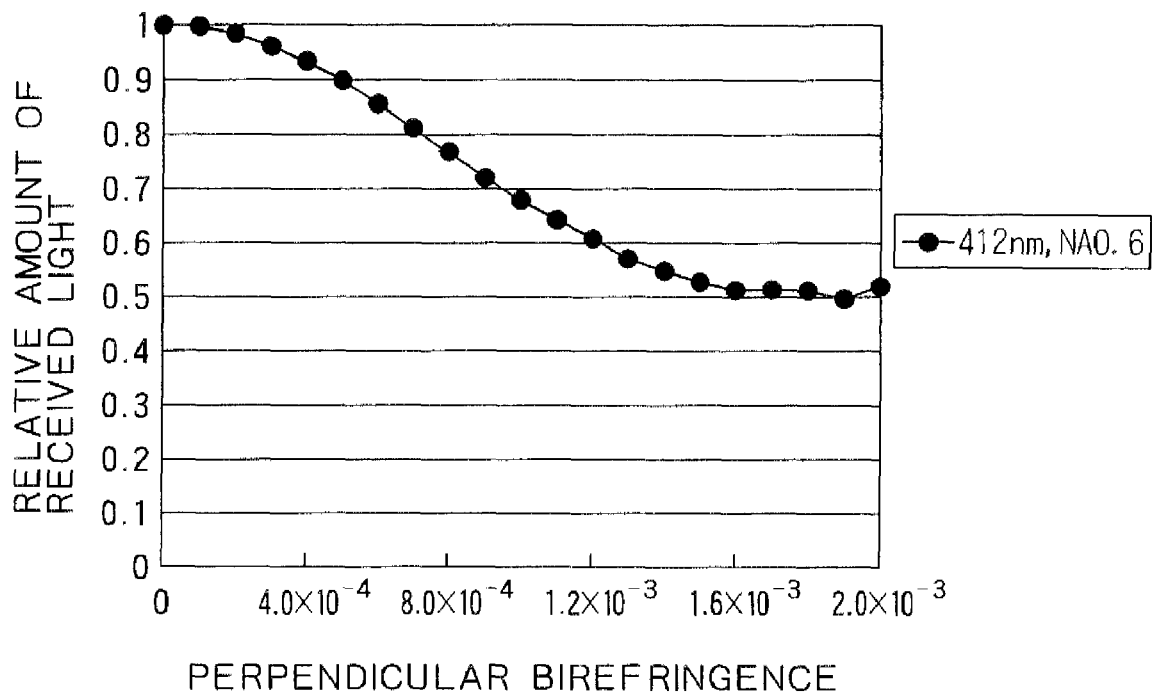
FIG. 8 is a diagram showing an example of computation of the relationship between perpendicular birefringence and the relative amount of received light.

FIG. 8 shows an example of computation of the relationship between perpendicular birefringence and the relative amount of received light. The horizontal axis in FIG. 8 indicates the perpendicular birefringence $\Delta n\perp$ and the vertical axis is the relative amount of received light ($L\perp$) obtained by normalizing the amount of received light L in case where only perpendicular birefringence is present by the amount of received light in case of no birefringence present. The calculation conditions are the wavelength of the light source being 412 nm and the numerical aperture (NA) of the objective lens being 0.6, which are equivalent to those of the embodiment of the optical information recording/reproducing apparatus according to the invention. The thickness of the protective layer of the optical recording medium is 0.6 mm. It is apparent that as the perpendicular birefringence increases, the relative amount of received light becomes smaller.

Figure 9:
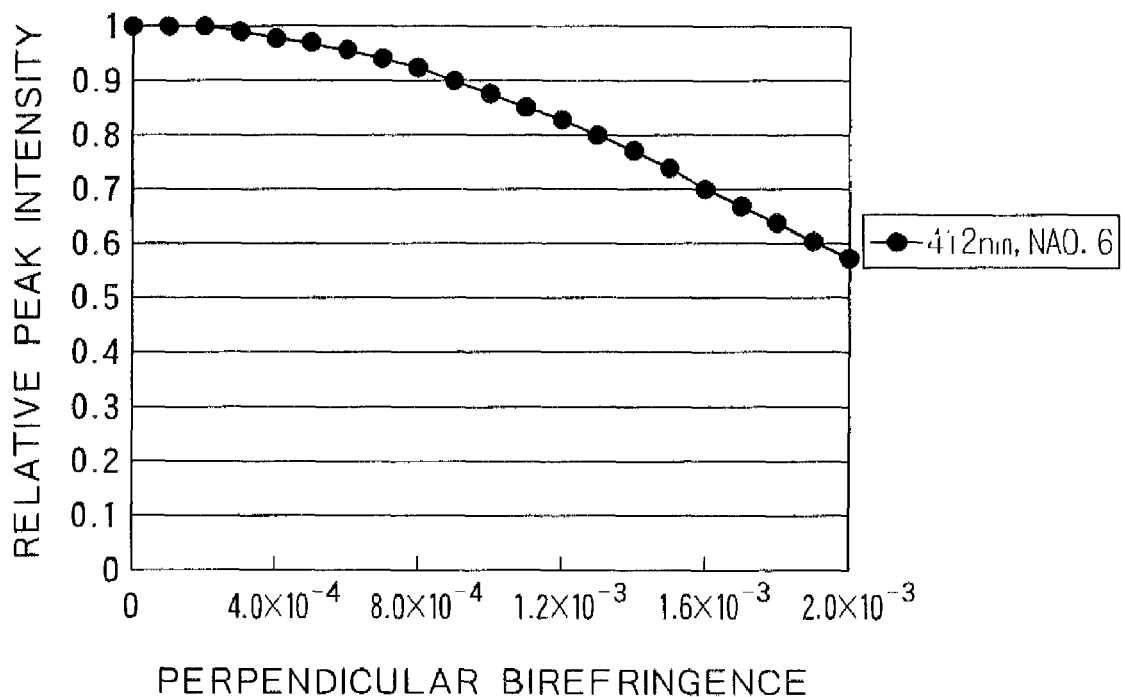
FIG. 9 is a diagram showing an example of computation of the relationship between perpendicular birefringence and the relative peak intensity.

FIG. 9 shows an example of computation of the relationship between perpendicular birefringence and the relative peak intensity. The horizontal axis in FIG. 9 indicates the perpendicular birefringence $\Delta n\perp$ and the vertical axis is the relative peak intensity obtained by normalizing the peak intensity P in case where only perpendicular birefringence is present by the peak intensity in case of no birefringence present. The calculation conditions are the wavelength of the light source being 412 nm and the numerical aperture (NA) of the objective lens being 0.6, which are equivalent to those of the embodiment of the optical information recording/reproducing apparatus according to the invention. The thickness of the protective layer of the optical recording medium is 0.6 mm. It is apparent that as the perpendicular birefringence increases, the relative peak intensity gets lower.

According to the DVD specifications, the allowance for perpendicular birefringence is not defined. Because a reduction in peak intensity caused by perpendicular birefringence increases the optical power needed at the time of recording, however, the allowance for perpendicular birefringence should be determined. A reduction in peak intensity is also caused by wavefront aberration of a focused spot besides the birefringence. With regard to the wavefront aberration of a focused spot, an allowance called the Marechal's criterion is defined as described on page 840 in "Optical Technology Handbook" (Asakura Bookstore). This is the allowance for RMS (Root Mean Square) wavefront aberration when the allowance for the peak intensity of a focused spot is 80% of that in case where there is no wavefront aberration, and is equivalent to about 0.07 $\lambda$ where $\lambda$ is the wavelength of the light source. With regard to perpendicular birefringence, therefore, it is reasonable to determine the allowance on the premise that the allowance for the peak intensity of a focused spot is 80% of that in case where there is no birefringence as in the case of the wavefront aberration. The allowance for perpendicular birefringence at this time is $\Delta n\perp \leq 1.3\times 10^{-3}$ as apparent from FIG. 9. This value, when converted to the allowance for relative amount of received light, becomes $L\perp \geq 0.57$ from FIG. 8.

That is, according to an optical recording medium whose protective layer has a thickness of 0.6 mm and whose recording and playback are carried out by an optical information recording/reproducing apparatus whose light source has a wavelength of 412 nm and whose objective lens has a numerical aperture (NA) of 0.6, the allowance for the relative amount of received light in case where there is perpendicular birefringence should be $L\perp \geq 0.57$ in order to suppress a reduction in peak intensity caused by perpendicular birefringence, which increases the optical power needed at the time of recording, and achieve the recording density of 8.2 Gbits/inch$^2$. The allowance for the relative amount of received light is basically the same for the case where the wavelength of the light source is set to 412 nm or shorter and the numerical aperture (NA) of the objective lens is set to 0.6 or higher to increase the recording density accordingly to 8.2 Gbits/inch$^2$ or greater. In the optical recording medium according to the embodiment of the invention, as the relative amount of received light satisfies this allowance and is $L\perp \geq 0.57$, it is possible to achieve the recording density of 8.2 Gbits/inch$^2$ necessary to record and play back high-definition moving pictures for 120 minutes.

Figure 10:
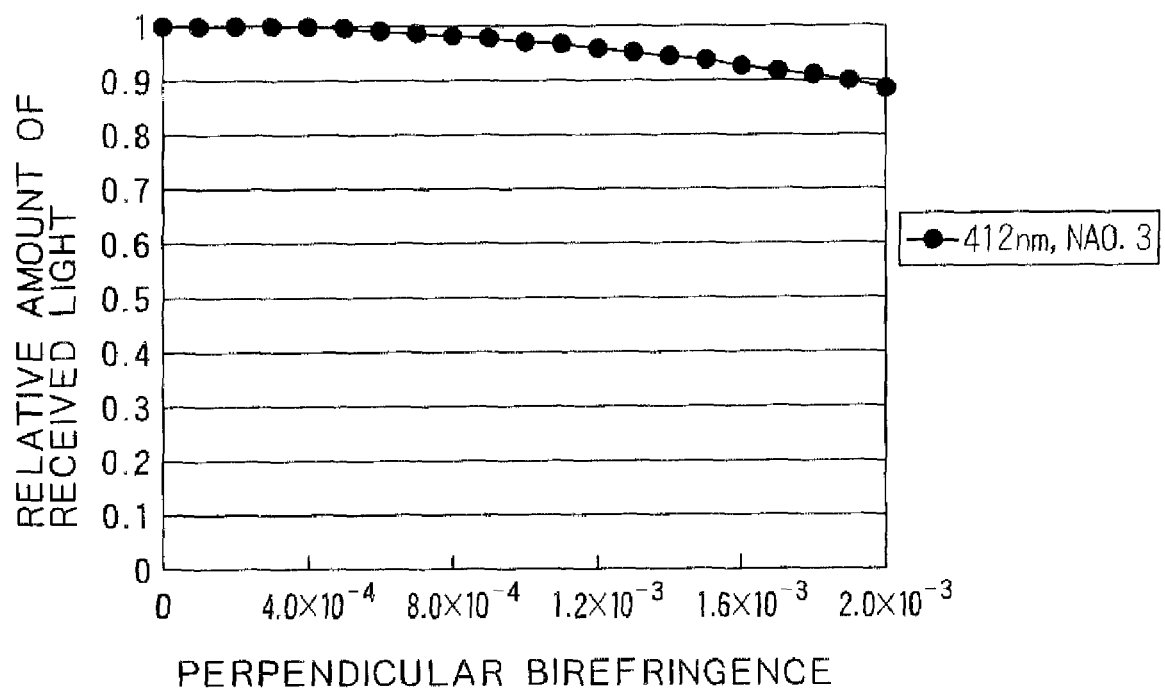
FIG. 10 is a diagram showing another example of computation of the relationship between perpendicular birefringence and the relative amount of received light.

FIG. 10 shows another example of computation of the relationship between perpendicular birefringence and the relative amount of received light. The horizontal axis in FIG. 10 indicates the perpendicular birefringence $\Delta n\perp$ and the vertical axis is the relative amount of received light ($L\perp$) obtained by normalizing the amount of received light L in case where only perpendicular birefringence is present by the amount of received light in case of no birefringence present. The calculation conditions are the wavelength of the light source being 412 nm and the numerical aperture (NA) of the objective lens being 0.3. The thickness of the protective layer of the optical recording medium is 0.6 mm. The numerical aperture (NA) of the objective lens 5 in the polarization optical system and the non-polarization optical system, which are used in the method of measuring the birefringence characteristic of the protective layer of the optical recording medium according to the embodiment of the invention, should be set to a value low enough that a reduction in the amount of received light caused by the influence of perpendicular birefringence in the polarization optical system can be neglected. If the numerical aperture (NA) of the objective lens 5 is set to 0.3, for example, a reduction in the amount of received light when the perpendicular birefringence is $1.3\times 10^{-3}$ or smaller is as small as about 5% and is thus negligible.

Figure 11:
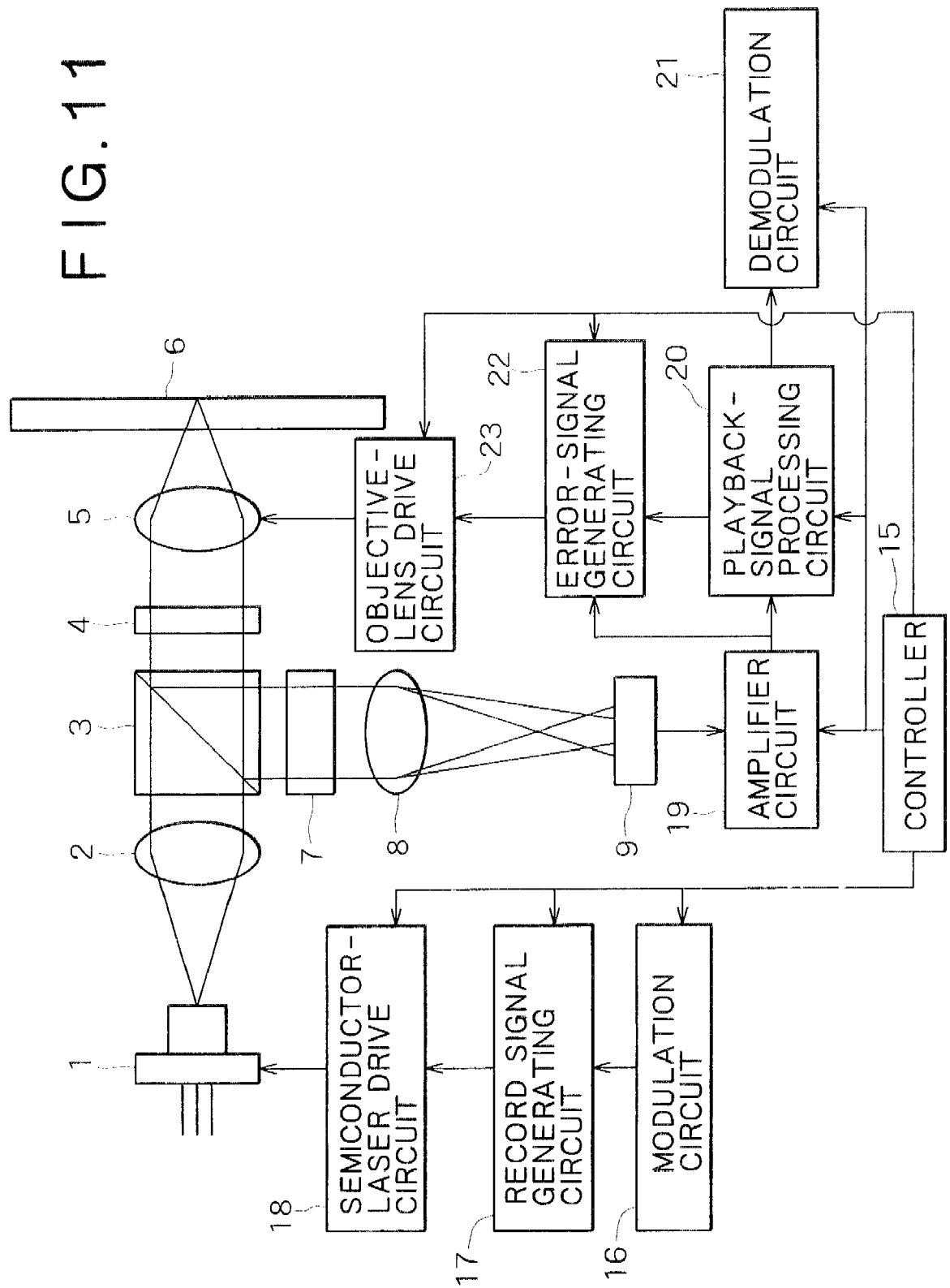
FIG. 11 is a diagram illustrating an optical information recording/reproducing apparatus according to one embodiment of the invention.

FIG. 11 shows an optical information recording/reproducing apparatus according to one embodiment of the invention. The structure of the optical system that guides output light from the semiconductor laser 1 to the disk 6 and the structure of the optical system that guides reflected light from the disk 6 to the photosensor 9 are the same as those in the polarization optical system shown in FIG. 3. The structure of the photosensor 9 is as illustrated in FIG. 5, and how to carry out arithmetic operations for the focus error signal and track error signal and sum signal are the same as those described earlier referring to FIG. 5. The wavelength of the semiconductor laser 1 is 412 nm and the numerical aperture (NA) of the objective lens 5 is 0.6. The thickness of the protective layer of the disk 6 is 0.6 mm and the recording density is 8.2 Gbits/inch$^2$. Further, the relative amounts of received lights on the disk 6 are $L\| \geq 0.79$ and $L\perp \geq 0.57$.

A modulation circuit 16 modulates data to be recorded on the disk 6 in accordance with modulation rules. A record signal generating circuit 17 generates a record signal to drive the semiconductor laser 1 in accordance with a recording strategy. A semiconductor-laser drive circuit 18 drives the semiconductor laser 1 by supplying the current corresponding to the record signal, generated by the record signal generating circuit 17, to the semiconductor laser 1 based on the record signal. Accordingly, data is recorded on the disk 6. An amplifier circuit 19 amplifies outputs from the individual light receiving sections of the photosensor 9. A playback-signal processing circuit 20 generates, equalizes and digitizes a playback signal (sum signal) based on the signals amplified by the amplifier circuit 19. A demodulation circuit 21 demodulates a signal, digitized by the playback-signal processing circuit 20, in accordance with demodulation rules. Accordingly, data is played back from the disk 6.

An error-signal generating circuit 22 generates a focus error signal and a track error signal based on the signals amplified by the amplifier circuit 19. An objective-lens drive circuit 23 drives the objective lens 5 by supplying the current corresponding to error signals, generated by the error-signal generating circuit 22, to an unillustrated actuator, based on the error signals. Further, the optical system excluding the disk 6 is driven in the radial direction of the disk 6 by an unillustrated positioner and the disk 6 is turned by an unillustrated spindle. Accordingly, focus, track, positioner and spindle servos are carried out.

The circuitry from the modulation circuit 16 to the semiconductor-laser drive circuit 18, which is associated with data recording, the circuitry from the amplifier circuit 19 to the demodulation circuit 21, which is associated with data playback, and the circuitry from the amplifier circuit 19 to the objective-lens drive circuit 23, which is associated with servos, are controlled by a controller 15.

According to the optical information recording/reproducing apparatus embodying the invention, the relative amount of received light satisfies the allowance and recording and playback are performed on an optical recording medium with $L\|\geq 0.79$ and $L\perp \geq 0.57$, thus making it possible to suppress a reduction in the amount of light received at the photosensor and a reduction in the peak intensity of a focused spot and achieve the recording density of 8.2 Gbits/inch$^2$ or higher which is required to record and play back high-definition moving pictures for 120 minutes.

What is claimed is:

1. An optical recording medium whose recording or playback is carried out at a recording density of 8.2 Gbits/inch$^2$ or higher using an optical information recording/reproducing apparatus having a light source with a wavelength of 412 nm or less and an objective lens with a numerical aperture of 0.6 or higher and which has a protective layer with a thickness of about 0.6 mm through which light is transmitted and in which $|\Delta n|\cdot 2d \leq 64$ nm where $|\Delta n|$ is a value of in-plane birefringence of said protective layer, which is defined as an absolute value of a difference between principal indexes of refraction associated with a radial direction and a tangential direction of said optical recording medium, and d is a thickness of said protective layer.

2. An optical information recording/reproducing apparatus that has a light source with a wavelength of 412 nm or less and an objective lens with a numerical aperture of 0.6 or higher and records or plays back, at a recording density of 8.2 Gbits/inch$^2$ or higher, an optical recording medium which has a protective layer with a thickness of about 0.6 mm through which light is transmitted and in which $|\Delta n|\cdot 2d \leq 64$ nm where $|\Delta n|$ is a value of in-plane birefringence of said protective layer, which is defined as an absolute value of a difference between principal indexes or refraction associated with a radial direction and a tangential direction of said optical recording medium, and d is said thickness of said protective layer.

* * * * *